US00PP13912P29

(12) United States Plant Patent
Vijverberg

(10) Patent No.: US PP13,912 P2
(45) Date of Patent: Jun. 24, 2003

(54) CHRYSANTHEMUM NAMED 'VYGOLD'

(75) Inventor: Arnold Vijverberg, 's-Gravenzande (NL)

(73) Assignee: Vyking Flowers B.V. (NL)

( * ) Notice: Subject to any disclaimer, the term of this patent is extended or adjusted under 35 U.S.C. 154(b) by 0 days.

(21) Appl. No.: 09/708,589

(22) Filed: Nov. 9, 2000

(51) Int. Cl.[7] ..... A01H 5/00
(52) U.S. Cl. ..... Plt./295
(58) Field of Search ..... Plt./295

(56) References Cited

PUBLICATIONS

Upov–Rom hit on 'Vygold', GTI Jouve Retrieval Software, Plant Variety Database 2001/04.*

* cited by examiner

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'VYGOLD' characterized by its small sized blooms with yellow ray-florets and brown disc florets.

3 Drawing Sheets

RELATED CULTIVARS

'VYGOLD' is related to 'VYMINI' (U.S. Plant Pat. No. 11,627). 'VYGOLD' is a sport of 'VYMINI'.

BACKGROUND OF THE INVENTION

'VYGOLD' is a product of a breeding and selection program which had the objective of finding color mutants of 'VYMINI'. The new plant of the present invention comprises a new and distinct cultivar of chrysanthemum plant that is a natural occurring sport of a parent chrysanthemum named 'VYMINI' (U.S. Plant Pat. No. 11,627). A comparison with Parent chrysanthemum 'VYMINI' is also made in this application. The new cultivar was discovered as a whole plant mutation in June 1996 by Nol Vijvergerg in a controlled environment (greenhouse) in 's-Gravenzande, Holland. The first act of asexual reproduction of 'VYGOLD' was accomplished when vegetative cuttings were taken from the initial selection in September 1996 in 's-Gravenzande, Holland.

SUMMARY OF THE INVENTION

The present invention is a new and distinct variety of chrysanthemum bearing small sized blooms with yellow ray-florets and brown disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
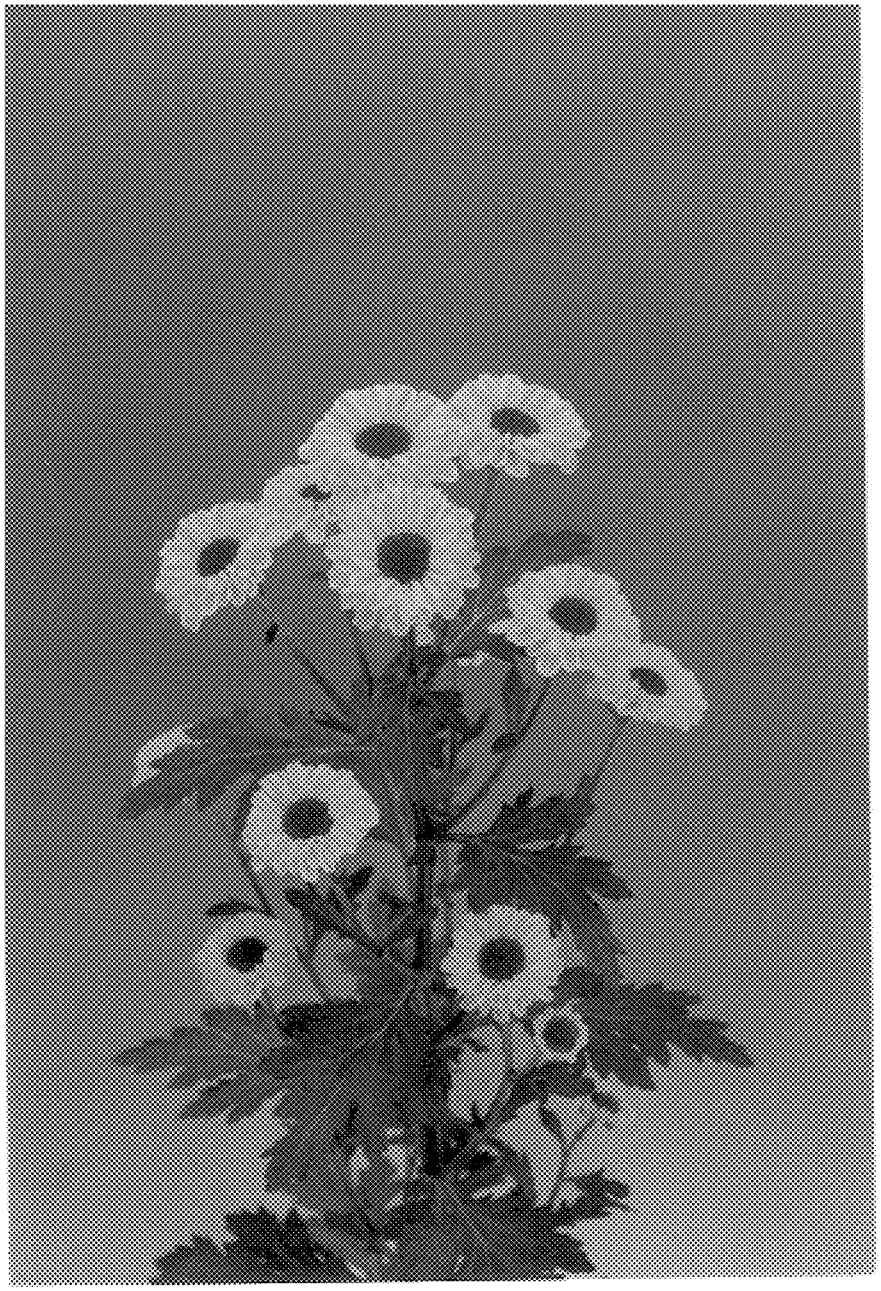
FIG. 1 shows a plant of the cultivar in full bloom.
Figure 2:
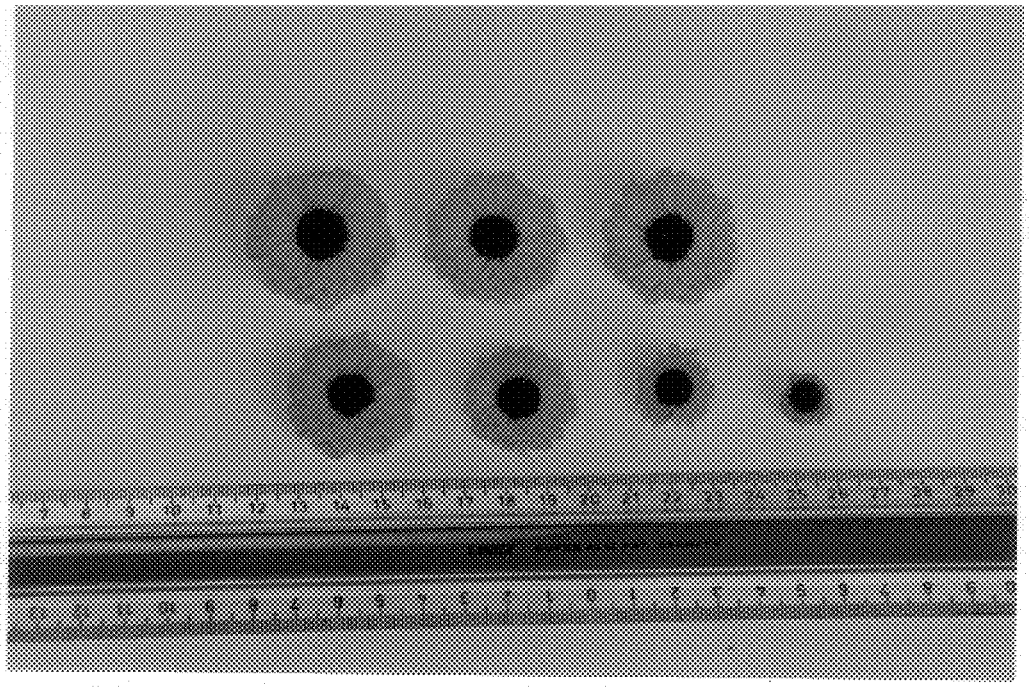
FIG. 2 shows the various stages of bloom of the new cultivar.
Figure 3:
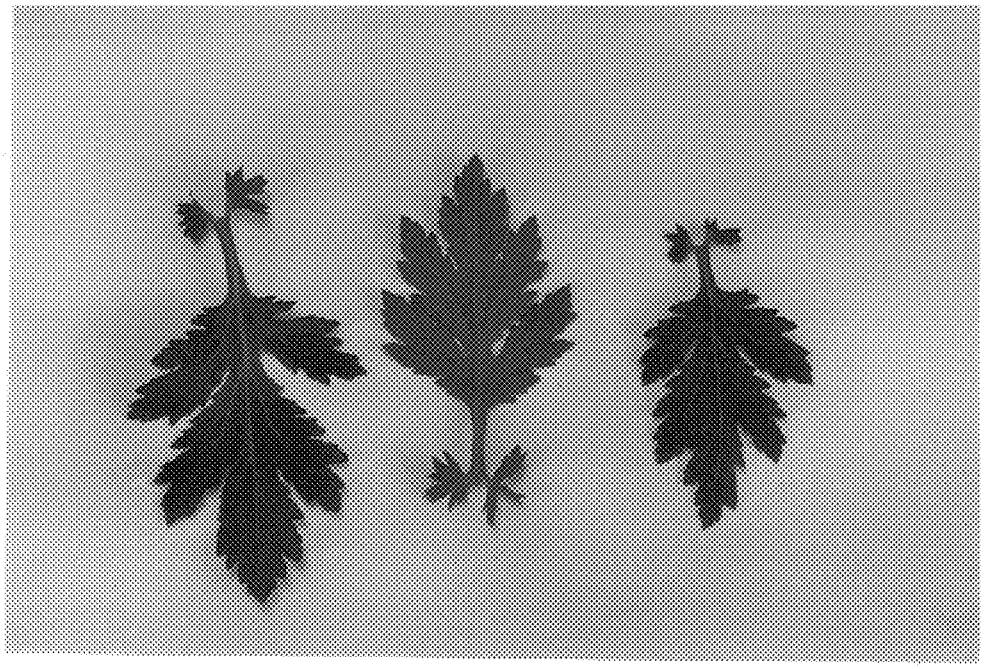
FIG. 3 shows the foliage of the new cultivar.

This new variety of chrysanthemum is of the botanical classification *Chrysanthemum morifolium*. The observations and measurements were gathered from plants grown in April/May in a greenhouse in 's-Gravenzande, Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 46 days. After the long day period to flowering growth retardants were applied 2 to 3 times in an average dose of 2.5 gram/liter water. No tests were done on disease or insect resistance or susceptibility. No tests were done on cold or drought resistance. This new variety produces small sized blooms with yellow ray-florets and brown disc-florets blooming on the plant for 3 weeks. This new variety of chrysanthemum has been found to retain its distinctive characteristics throughout successive propagations however the phenotype may vary significantly with variations in environment such as light intensity and temperature. To show the phenotype as described 'VYGOLD' can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

The variety 'VYGOLD' is a natural mutant of 'VYMINI'. When 'VYGOLD' and 'VYMINI' are being compared the following differences and similarities are noticed: The differences of 'VYGOLD' and 'VYMINI' are (1) flower-size and color (2) flower-form, (3) growth and (4) flower-count for which characteristics 'VYGOLD' has been selected out of 'VYMINI'. All other characteristics of 'VYMINI' and 'VYGOLD' are similar.

(1) Flower-size: The flower of 'VYGOLD' is larger then the flower of 'VYMINI' and the flower-disc of 'VYGOLD' is darker brown (2) Flower-form: 'VYGOLD' has a more "tidy" flower as 'VYMINI' and the petals are somewhat longer. (3) The growth of 'VYGOLD' is more vigorous than the growth of 'VYMINI'. (5) The flower-count of 'VYGOLD' is lower than the flower-count of 'VYMINI'.

The following is a description of the plant and characteristics that distinguish 'VYGOLD' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of Cultivar 'Vygold'

Bud:
*Size.*—Medium, cross-section 1.2 cm height 1.2 cm.
*Outside color.*—Yellow 13 B.
*Involucral bracts.*—2 rows, length 7 mm, width 3 mm.
*Involucral bracts among disc-florets.*—Not present.
*Involucral bracts color.*—Yellow-green 146 B.

Bloom:
*Type.*—Single.
*Height.*—Flat, 1.0–1.5 cm.
*Size.*—Small.
*Fully expanded.*—3.5–4.0 cm.
*Number of blooms per stem.*—Average of 12–15.
*Performance on the plant.*—3 weeks.
*Seeds (if crossed).*—Produced in small quantities, ovate shaped. Grey-brown 199 A, 1.5 mm in length.
*Fragrance.*—Typical chrysanthemum, slight.

Color:
*Center of the flower (disc-florets).*—Immature brown 200 A. Mature brown 200 C.
*Color of upper surface of the ray-florets.*—Yellow 9 A.
*Color of the lower surface of the ray-florets.*—Yellow 7 B.
*Tonality from distance.*—A spray mum with yellow flowers and a brown disc.
*Color of the upper surface after aging of the plant.*—Ray-florets yellow 9 A, disc-florets brown 200 C.

Ray florets:
*Texture.*—Upper and under side smooth.
*Number.*—35–38 (2 rows).
*Cross-section.*—Concave (one keel).
*Longitudinal axis of majority.*—Straight.
*Length of corolla tube.*—Short, 0.4 cm.
*Ray-floret margin.*—Entire.
*Ray-floret length.*—1.3–1.6 cm.
*Ray-floret width.*—0.4–0.6 cm.
*Ratio length/width.*—Medium.
*Shape of tip.*—Rounded sometimes dentate.

Disc florets:
*Disc diameter.*—1.0 cm.
*Distribution of disc florets.*—Numerous clearly visible at all stages of flowering.
*Shape.*—Tubular.
*Color.*—Yellow-green 144 A, brown 200 A at the tip.
*Receptacle shape.*—Conical raised.

Reproductive organs:
*Stamen (present in disc florets only).*—Thin, 3 mm in length.
*Number of stamen.*—4.
*Stamen color.*—Yellow-green 144 A.
*Pollen.*—Not present.
*Styles (present in both ray and disc florets).*—Thin.
*Style color.*—Yellow-green 144 A.
*Style length.*—4 mm.
*Stigmas color.*—Yellow-green 144 A.
*Stigma width.*—1 mm.
*Ovaries.*—Enclosed in calyx.

Plant:
*Form.*—A spray mum meant for erect culture.
*Growth habit.*—Upright.
*Growth rate.*—Slow.
*Height.*—75–100 cm.
*Internodes.*—2.0–2.5 cm.
*Spray formation.*—Corymbiform.
*Stem color.*—Yellow-green 146 B.
*Stem strength.*—Strong.
*Stem brittleness.*—Present.
*Stem anthocyanin coloration.*—Present, mainly at the base of the stem a thin layer of greyed-red 181 A.
*Peduncle length.*—Near the top 6 cm, near the middle 12 cm, near the bottom 16 cm.
*Peduncle color.*—Yellow-green 146 B.
*Flowering response (photo-periodic controlled crop, not natural season).*—46 days.

Foliage:
*Color of mature leaves.*—Upper side yellow-green 144 A. Under side yellow-green 144 B.
*Color of immature leaves.*—Upper side yellow-green 144 A. Under side yellow-green 144 B.
*Size.*—Medium; length 7 cm, width 4 cm.
*Quantity (number per single stem).*—30–35.
*Shape.*—Incurved.
*Texture upper side.*—Fleshy and glabrous.
*Texture under side.*—Pubescent.
*Venation arrangement.*—Palmate.
*Shape of the margin.*—Crenated.
*Shape of base of sinus between lateral lobes.*—Round.
*Margin of sinus between lateral lobes.*—Converging.
*Shape of base.*—Truncate.
*Apex.*—Mucronate.

Differences with the comparison Varieties

| | 'VYGOLD' | 'VYMINI' |
|---|---|---|
| Flower size | 3.5–4.0 cm | 3.0–3.5 cm |
| Flower count per single stem | Average of 12–15 | Average of 22–25 |
| Growth rate | Slow | Very slow |

I claim:

1. A new and distinct variety of chrysanthemum plant as described and illustrated.

* * * * *